United States Patent
Roberts et al.

(10) Patent No.: US 6,562,352 B1
(45) Date of Patent: *May 13, 2003

(54) VACCINE COMPOSITIONS FOR MUCOSAL DELIVERY

(75) Inventors: Mark Roberts, London (GB); Gordon Dougan, London (GB)

(73) Assignee: Medeva Holdings, B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/963,129

(22) Filed: Oct. 28, 1997

Related U.S. Application Data

(63) Continuation of application No. 08/325,413, filed as application No. PCT/GB93/00880 on Apr. 28, 1993, now abandoned.

(30) Foreign Application Priority Data

Apr. 28, 1992 (GB) .............................................. 9209118

(51) Int. Cl.$^7$ .......................... A61K 39/10; A61F 13/00
(52) U.S. Cl. ................... 424/240.1; 424/253.1; 424/254.1; 424/434; 424/435
(58) Field of Search .......................... 424/240.1, 253.1, 424/254.1, 434, 435

(56) References Cited

FOREIGN PATENT DOCUMENTS

| EP | 0 209 281 A1 | 1/1987 |
|----|--------------|--------|
| EP | 0267998 A1 | 5/1988 |
| EP | 0462534 A2 | 12/1991 |
| EP | 0462534 A3 | 12/1991 |
| EP | 0484621 A2 | 5/1992 |
| JP | 63002932 A | 1/1988 |
| WO | WO 90/13313 | 11/1990 |
| WO | WO 90/15871 A1 | 12/1990 |
| WO | WO 92/15689 | 9/1992 |

OTHER PUBLICATIONS

Medline Abs. #85 0528 26, Ambrosch et al.*
Lazar et al (Molecular & Cellular Biology vol. 8, No. 3, Mar. 1988 pp 1247–1252).*
Burgess et al (Journal of Cell Biology vol. 111, Nov. 1990 pp. 2129–2138).*
Salgaller et al (Cancer Immunol. Immunother. vol. 39, 1994 pp 105–116).*
Roberts, Mark et al., "Construction and Characterization In Vivo of *Bordetella pertussis* aroA Mutants"; Infection and Immunity, Mar. 1990, pp. 732–739.
Wigley, F.M. et al., "Aerosol Immunization of Humans with Tetanus Toxoid"; The Journal of Immunology, Nov. 1969, pp. 1096–1098.
Waldman, M.D., Robert H. et al., "Utilization of the Secretory Immunologic System for Protection Against Disease"; U.S. Department of Health, Education, and Welfare—Proceedings of a Conference, Dec. 10–13, 1969, Vero Beach, FLA, pp. 129–147.
Chatfield, S.N. et al., "Construction of a genetically defined *Salmonella typhi* Ty2 aroA, aroC Mutant for the Engineering of a Candidate Oral Typhoid–Tetanus Vaccine"; Vaccine, vol. 10, Issue 1, 1992, pp. 53–60.
Fairweather, Neil F. et al., "Oral Vaccination of Mice against Tetanus by Use of a Live Attenuated *Salmonella* Carrier"; Infection and Immunity, May 1990, pp. 1323–1326.
PCT Written Opinion dated Feb. 21, 1994 by C. Sherrington, Authorized Officer, re:International Application No. PCT/GB93/00880.
Chatfield et al (1992) Vaccine 10:53–60
McImowat (1996) Chemistry & Industry, Nov. :876–880.
Newcomb & DeVald (1969) Fed Proc 28:765.
Baljer (1975) 14$^{th}$ Congress of the International Association of Biological standardization, 33:63–71
Sheppard et al (1984) Infection & Immunity 43:710–714.

* cited by examiner

*Primary Examiner*—Mark Navarro
(74) *Attorney, Agent, or Firm*—Wolf, Greenfield & Sacks, P.C.

(57) ABSTRACT

The invention provides the use of an antigen which is a mucosally immunogenically active substance comprising the 50 kD C fragment of tetanus toxin, an immunogenic fragment thereof, or a derivative thereof formed by amino acid deletion, substitution or insertion for the manufacture of a vaccine composition for administration to a mucosal surface to induce an immune response in the mucosal surface against tetanus infection. The Vaccine composition preferably contains the P.69 outer membrane protein of *B. pertussis*, and *B. pertussis* filamentous haemaglutiuin. The invention also provides vaccine compositions per se and a method of treating tetanus and optionally whooping cough using the vaccine compositions.

16 Claims, 4 Drawing Sheets

VACCINE COMPOSITIONS FOR MUCOSAL DELIVERY

Figure 1:
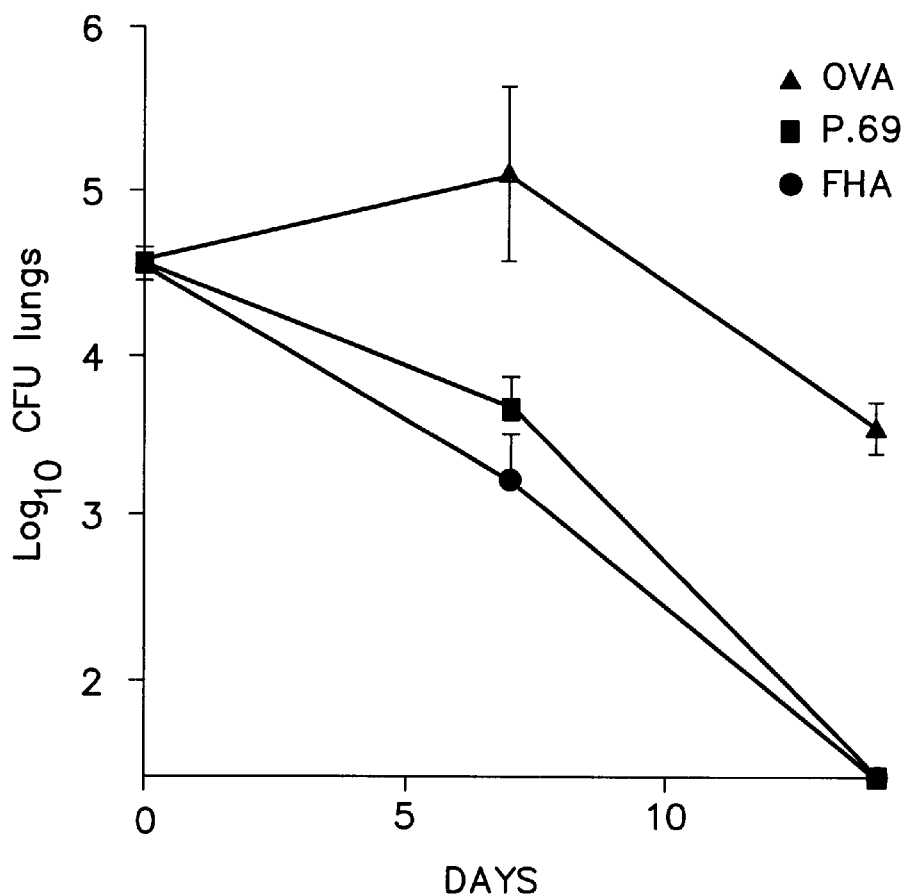
Figure 2A:
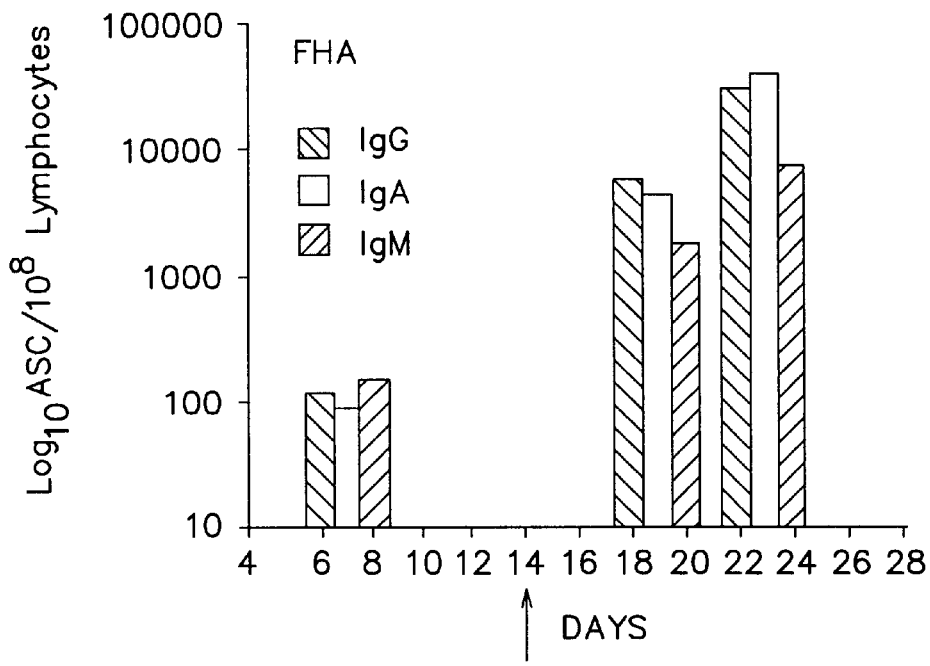
Figure 2B:
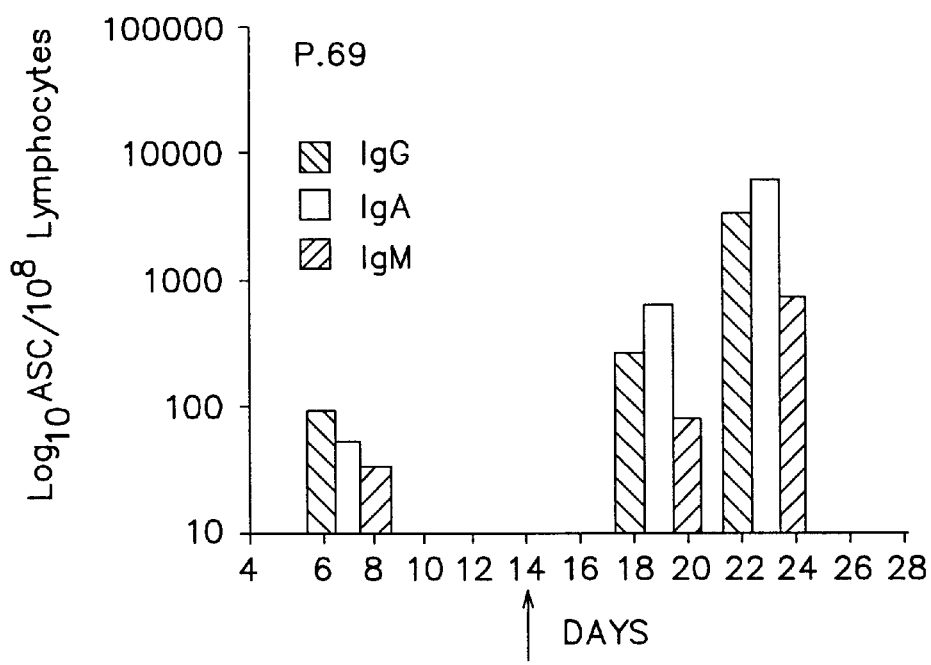
Figure 2C:
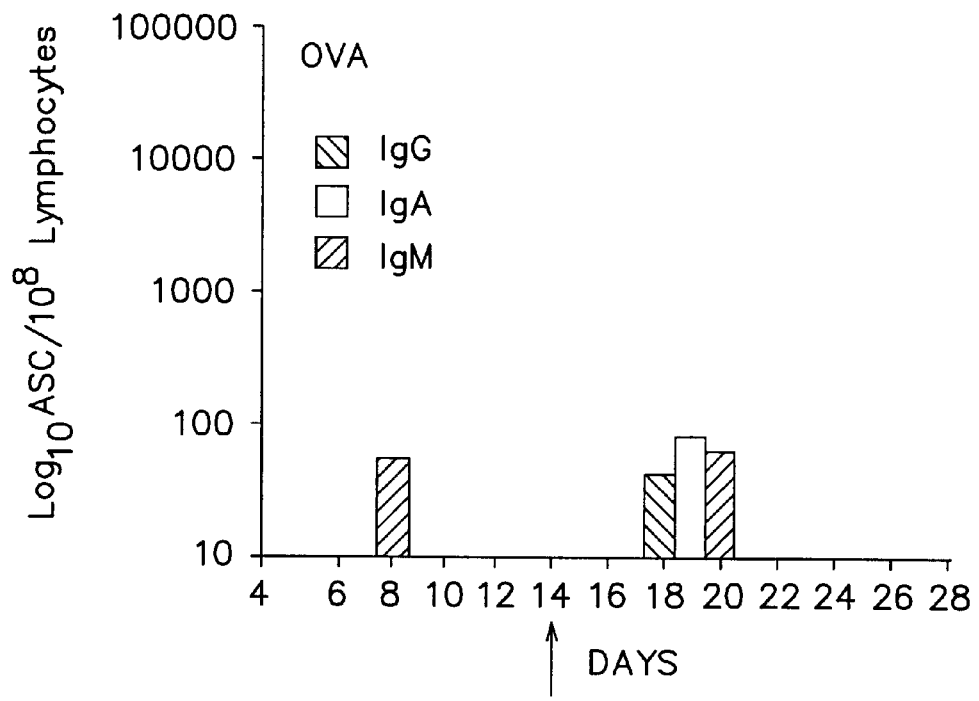
Figure 3:
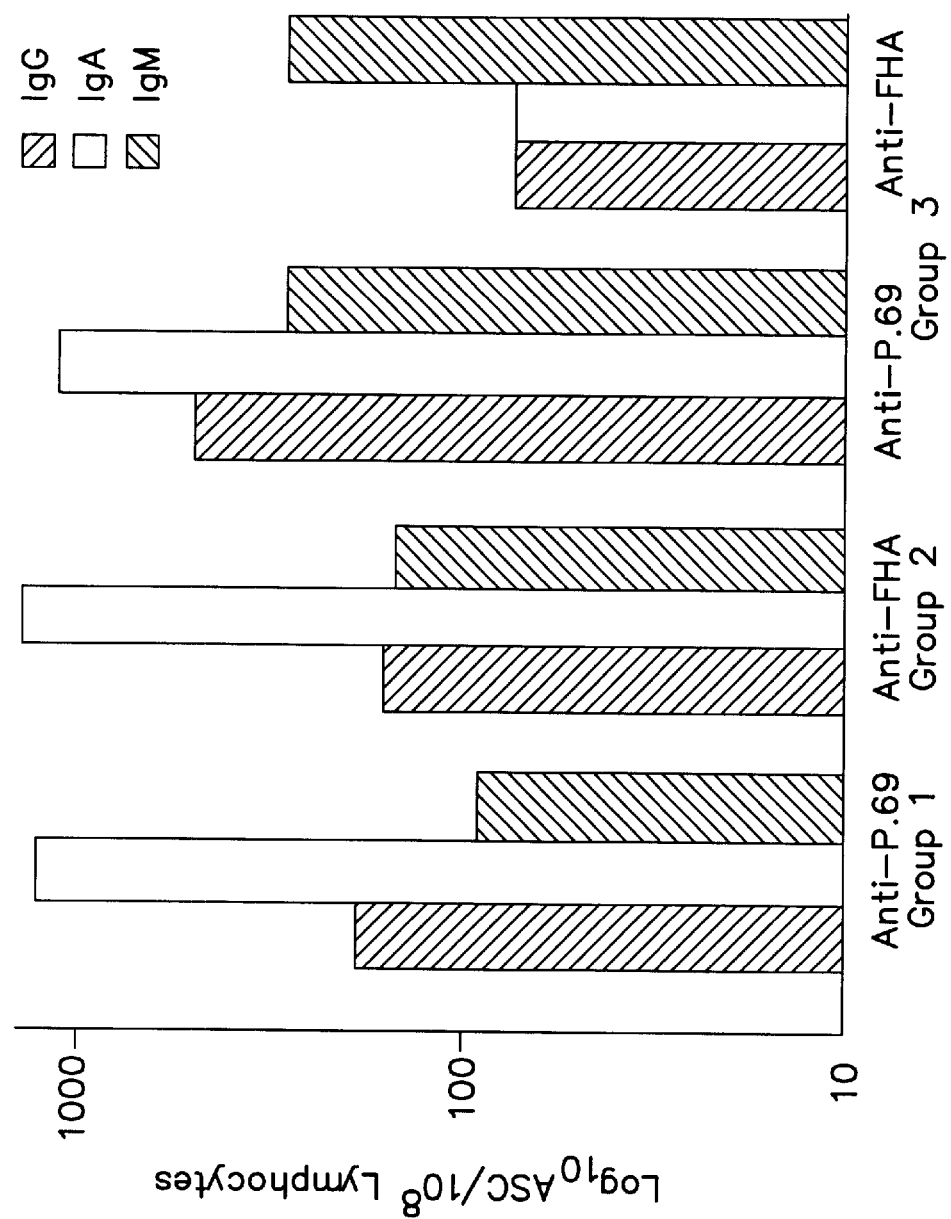

This application is a continuation of Ser. No. 08/325,413, filed Dec. 28, 1994, now abandoned, which is a national phase application of PCT/GB93/00880, filed Apr. 28, 1993.

BACKGROUND OF THE INVENTION

The present invention relates to vaccine compositions for delivery to mucosal surfaces, and to a method of inducing, in a mammal, an immune response to an antigen or a mixture of antigens by delivering the antigen or mixture of antigens to a mucosal surface of the mammal.

More particularly, the present invention relates to vaccine compositions for inoculating a mammal such as a human against tetanus and B. pertussis infections.

It has long been the practice of clinicians to immunise human infants against a variety of common diseases by means of mixed vaccines which are directed against a plurality of diseases. For example, multiple-component vaccine compositions directed against diphtheria, tetanus and whooping cough have been available for a considerable number of years. Such vaccines have hitherto been administered by injection. The advantages of multiple-component vaccines are readily apparent in that the patient (usually an infant) is subjected to a much smaller number of potentially distressing injections than would otherwise be the case.

The majority of infectious diseases are initiated by contact with a mucosal surface. The infecting agent may remain at or within the mucous membranes during the course of the infection or may penetrate into the body and localise at other sites. The importance of the mucous membranes in the first line of defence against infectious disease can be gleaned from the fact that 90% of the lymphocytes of the body underlie such surfaces. Priming mucosal surfaces by immunisation so that they respond vigorously and effectively control pathogenic organisms they encounter would be advantageous. Unfortunately traditional immunisation regimes are ineffective at eliciting mucosal responses. The systemic and local (mucosal) immune systems appear to be compartmentalised and in general do not impinge on one another; that is parenteral immunisation with non-living vaccines stimulates mucosal immune responses weakly if at all. Mucosal immunisation (oral or intranasal) can evoke serum antibodies but this is usually less effective than parenteral immunisation. The immunocytes of the different mucous membranes form a vast intercommunicating network, termed the common mucosal immune system, such that topical immunisation of one surface (e.g. the gastrointestinal tract) may lead to an immune response at that surface and also distance surfaces such as the respiratory tract.

Manclark and Shahin (U.S. patent application Sre. No. 07/532,327, now abandoned, filed May 6, 1990—available through the US Department of Commerce, National Technical Information Service, Springfield, Va. 22161, U.S.A.)—have described the intranasal and intraduodenal administration of filamentous hemagglutinin (FHA) obtained from Bordetella pertussis and have illustrated that FHA is an effective mucosal immuogen. Manclark and Shahin speculated in U.S. Ser. No. 07/532,327, now abandoned, that the 69-kD outer membrane protein (P69) of B. pertussis would also be an effective mucosal immunogen, but presented no experimental data to show that this was the case.

The fact that there are very few mucosal vaccines commercially available indicates that there are problems with developing such vaccines Many non-living soluble antigens, particularly those used traditionally by immunologists, such as ovalbumin (OVA) and Keyhole Limpet Haemocyanin (KLH), are poor mucosal immunogens. Large doses of such antigens are necessary to induce any responses but large doses can also cause tolerance in the individual to subsequent parenteral exposure to antigen, a condition known as oral tolerance. Some microbial components such as the cholera toxin (CT) or E. coli heat-labile toxin (LT) or the non-toxic binding portions of these toxins (CT-B and LT-B) have been found to be potent mucosal immunogens eliciting strong secretary and circulating antibodies, but the reason why such molecules are good mucosal immunogens has not yet been fully elucidated. One property that may be important is the ability of these molecules to bind to mucosal epithelial cells via certain surface receptors, although it has been found in studies by others that there is not necessarily a correlation between the ability of an antigen to bind to eucaryotic cells and its mucosal immunogenicity.

Thus, as far as we are aware, there is currently no way of predicting with any certainty whether a given antigen will possess good mucosal immunogenicity.

SUMMARY OF THE INVENTION

We have now found that certain molecules make excellent mucosal immunogens and such components can be utilised in the development of a mucosally (intranasally or orally) delivered vaccine against the diseases whooping cough and tetanus. In particular, we have found that the P69 outer membrane protein (P69—also known as pertactin) from B. pertussis and the non-toxic immunogenic 50 Kd portion of tetanus toxin (C-Fragment) from C. tetanii are highly immunogenic when given intranasally. C-Fragment and P.69 were generated by DNA recombinant technology. Recombinant C-Fragment and P.69 produced from E. coli and yeast have been demonstrated to be immunogenic and protective in mice, see M. Roberts et al, Recombinant P.69/pertactin: imminogenicity and protection of mice against Bordetella pertussis infection; Vaccine 10, 43 (1992); and see also N. F. Fairweather et al, Infection and Immunity, 55, 2541 (1987).

In a first aspect, the invention provides the use of a mucosally immunogenically active substance comprising the 50 kD C fragment of tetanus toxin, an immunogenic fragment thereof, or a derivative thereof formed by amino acid deletion, substitution or insertion, for the manufacture of a vaccine composition for immunising a patient against tetanus infection.

In one particular embodiment of the invention, there is provided the use of a mixture of antigens for the manufacture of a vaccine composition for administration to a mucosal surface to induce an immune response in the mucosal surface against each of the said antigens, the mixture of antigens comprising:

(a) a mucosally immunogenically active substance comprising the 50 kD C fragment of tetanus toxin, an immunogenic fragment thereof, or a derivative thereof formed by amino acid deletion, substitution or insertion; and (b) a mucosally immunogenically active substance comprising the P.69 outer membrane protein of B. pertussis; an immunogenic fragment thereof, or a derivative thereof formed by amino acid deletion, substitution or insertion.

In a preferred embodiment the invention provides the use of a mixture of antigens as hereinbefore defined but wherein said mixture comprises in addition to (a) and (b);

(c) a mucosally immunogenically active substance comprising *B. pertussis* filamentous haemaglutinin, an immunogenic fragment thereof, or a derivative thereof formed by amino acid deletion, substitution or insertion.

In a further aspect, the invention provides a vaccine composition for application to a mucosal surface, the composition comprising antigen (a) or a mixture of antigens as hereinbefore defined and a pharmaceutically acceptable carrier.

In another aspect the invention, provides a method of immunising a host such as a mammal, (e.g. human) against infection, which method comprises administering an effective amount of antigen (a), or a mixture of antigens as hereinbefore defined, directly to a mucosal surface in the host to induce in said mucosal surface an immune response to each said antigen.

The mucosal delivery compositions of the present invention can be formulated, for example, for delivery to one or more of the oral, gastro-intestinal, and respiratory (e.g. nasal and bronchial) mucosa.

Where the composition is intended for delivery to the respiratory (e.g. nasal or bronchial) mucosa, typically it is formulated as an aqueous solution for administration as an aerosol or nasal drops, or as a dry powder, e.g. for inhalation.

Compositions for administration as nasal drops may contain one or more excipients of the type usually included in such compositions, for example preservatives, viscosity adjusting agents, tonicity adjusting agents, buffering agents and the like.

The antigenic preparations of the present invention may also take the form of compositions intended to deliver the mixture of antigen to mucosal surfaces in the gastrointestinal tract. It is preferred that such compositions are provided with means for preventing degradation of the antigens by the gastric juices. For example, the compositions may take the form of capsules, e.g. microcapsules, in which the antigens are retained within a protective matrix or coating formed from an appropriate protective polymer such as a poly (glycolide), poly (lactide-co-glycolide), polyactyl starch, or pH-dependent coatings such as the polyacrylates or hydroxypropylmethyl cellulose phthalate.

The antigens may take the form of the tetanus toxin C fragment per se, the P.69 protein per se, or the *B. pertussis* haemaglutinin per se. Or it may take the form of a larger molecule containing one or more of the aforesaid antigens, immunogenically active fragments thereof, or derivatives formed by amino acid deletion, substitution and insertion, provided that the larger molecule is immunogenically active when administered directly to the mucosa.

The antigen or mixture of antigens typically is selected such that it is non-toxic to a recipient thereof at concentrations employed to elicit an immune response.

In one embodiment, two more of the antigens forming the mixture may be presented in a single molecule. Such a molecule may be prepared by recombinant methods by preparing a DNA construct containing genes coding for two or more of the antigens and expressing in a suitable host in accordance with known methods.

The individual antigenic substances making up the compositions of the invention may each also act as carriers for one or more other antigens. For example, an antigen such as the P.69 outer membrane protein or C-Fragment may be coupled to another antigen, and examples of such "other" antigens include Haemophilus group B and meningococcal polysaccharide antigens.

In order to enhance the mucosal immunogenicity of the mixture of antigens or any component antigen thereof or appropriate immunogenic fragments thereof, they may be incorporated into appropriate carriers, for example virosomes, or the antigens or immunogenic fragments thereof may be expressed in suitable attenuated carrier strains of Salmonella. Immunogenicity may also be enhanced by incorporating appropriate mucosal adjuvants such as cholera toxin or *E. coli* heat-labile toxin, genetically detoxified variants thereof or their binding (B) sub-units in the vaccine.

The vaccine composition may optionally contain another mucosally immunogenically active portion of the tetanus toxin molecule. In addition, the mixed vaccine may contain one or more further mucosally immunogenically active antigens.

In one embodiment, the vaccine composition may, in addition to non-toxic immunogenic forms of tetanus toxin and pertussis antigens, contain non-toxic immunogenic forms of diphtheria toxin and immunogenic forms of *Haemophilus influenzae* group B polysaccharide (HiB), thereby providing a mucosal diphtheria-tetanus-pertussis (DTP) vaccine or DTPHiB vaccine.

The P.69 outer membrane protein of *B. pertussis* is a protein of approximately 51 KD molecular weight; see A. J. Makoff et al, "Protective surface antigen P.69 of *Bordetella pertussis*: its characteristics and very high level expression in *Escherichia coli*", *Bio-Technology*, 8, 1030 (1990).

It can be prepared and isolated according to the method disclosed in P. Novotny et al: The Journal of Infectious Diseases, 164, 114 (1991), or recombinant material prepared from *E. coli* by the method given in the article by A. J. Makoff et al referred to above. It can bind to eukaryotic cells.

Purified *B. pertussis* filamentous haemaglutinin usually contains polypeptides of differing molecular weight ranging from 98–220 KD, and can be isolated and purified from cell culture supernatants of *B. pertussis*, for example as described in the article by P. Novotny et al referred to above. The filamentous haemaglutinin is able to bind to eukaryotic cells and cause haemaglutination of sheep erythrocytes.

The C fragment of tetanus toxin is a peptide of approximately 50 KD molecular weight which can be isolated and purified form *E. coli* by the method described in A. J. Makoff et al., *Bio/Technology*, 7, 1043 (1989). The C fragment is characterised by an ability to bind the eukaryotic cells possessing the trisialoganglioside $G_T 16$ and by an ability to elicit protection in mice against lethal challenge with tetanus toxin.

The antigenic molecules of the present invention can be prepared by isolation and purification from the organisms in which they occur naturally, or they may be prepared by recombinant techniques and expressed in a suitable host such as *E.coli* in known manner. When prepared by a recombinant method or by synthesis, one or more insertions, deletions, inversions or substitutions of the amino acids constituting the peptide may be made. Each of the aforementioned antigens is preferably used in the substantially pure state. The quantity of the mixture of antigens administered will depend, in part, upon the purity of the individual antigens. Thus, for a substantially pure form of the P.69 outer membrane protein, a dose in the range from about 1–100 microgrammes/dose typically would be administered to a human, the actual amount depending on the immunogenicity of the preparation in humans when applied to mucosal surfaces.

For a substantially pure form of the *B. pertussis* filamentous haemaglutinin, and the 50 KD C fragment of tetanus toxin, a typical dose range would be of the order given above in respect of P.69 protein. In a typical immunisation regime employing the antigenic preparations of the present invention, the vaccine may be administered in several doses (e.g. 1–4), each dose containing 1–100 microgrammes of each antigen. The immunisation regime may involve immunisation purely by the mucosal route or by a combination of mucosal and parenteral immunisation. The dosage will in general depend upon the immunogenicity of the different antigens when applied to the respiratory or gastrointestinal tracts of humans.

The invention will now be illustrated in greater detail by reference to the specific embodiments described in the following examples.

The examples are intended to be purely illustrative of the invention and are not intended to limit its scope in any way.

BRIEF DESCRIPTION OF THE FIGURES

FIG. 1 illustrates the growth of *B. pertussis* in the lungs of intranasally immunised mice. Mice were immunised intranasally with two doses of antigen on day 0 and day 29 and then aerosol challenged with *B. pertussis* 14 days later (day 43). The counts represent the means of 4 pairs of lungs±SEM.

FIG. 2 illustrates the local immune response in the lungs of mice in response to intranasal immunisation and challenge. Lymphocytes were purified from the lungs of groups of mice after intranasal immunisation and aerosol challenge and the number of cells secreting antibody to the immunising antigen was determined by the ELISPOT assay. Counts represent the response of lymphocytes pooled from 4 mice.

FIG. 3 illustrates the primary antibody response to pertussis antigens in the lungs of mice following aerosol challenge. Lymphocytes from Lungs removed 10 days after aerosol challenge were assayed for antibody production against P69 or FHA. Mice immunised with one antigen were tested against the other antigen. Counts represent the response of lymphocytes pooled from groups of 4 mice.

DESCRIPTION OF THE PREFERRED EMBODIMENTS

EXAMPLE 1

Pertussis Components

Mice were immunised with 12 $\mu$g of either P.69, FHA or OVA on day 1 and day 29. Mice were then aerosol challenged with *Bordetella pertussis* on day 43 (14 d post boost). Lungs were removed from groups of mice at periods after challenge, homogenised and viable bacterial counts performed to determine the growth of *B. pertussis* in the respiratory tract. The results are shown in FIG. 1.

Bacteria increased in numbers in the lungs of control mice (OVA) during the first seven days. In contrast, in both P.69 and FHA immunised animals bacterial number declined during this period and at the day 7 time point the levels of bacteria in the lungs of immunised mice were only 1–4% of those in the control group. By day 14 bacteria had almost cleared from the lungs of the immunised mice but were still present in large numbers in the OVA immunised mice.

The local immune response in the lungs of mice was analysed by enumerating cells secreting antibody against FHA, P.69 or OVA amongst lymphocytes isolated from the lungs of mice by "ELISPOT". There were low numbers of antibody secreting cells (ASC) producing antibody against the immunising antigens after the second (FIG. 2). Following aerosol challenge of ASC in the lungs of mice immunised with FHA or P.69, but not OVA, increased by several orders of magnitude (FIG. 2). Cells secreting antibody of IgG, IgA and IgM isotypes were detected.

The increase in ASC following aerosol challenge may represent a primary response to the antigens present in the challenge organisms or a boost of the response in immunised mice. To see which of these options was correct, lung lymphocytes were screened against antigens which the mice had not encountered until challenge (FHA immunised mice were tested against P.69 etc). As can be seen from FIG. 3, the responses were similar in all mice and comparisons with the same time point (d23) in FIG. 1 shows that prior intranasal immunisations boost the response several fold.

The serum response was studied using ELISA and the results are shown in Table 1 below:

TABLE 1

Serum anti-pertussis antibody response of intranasally immunised mice

| | ANTIBODY TITRE[a] Days post-immunisation | | | | | |
|---|---|---|---|---|---|---|
| | 8 | | 20 | | 24 | |
| Group | FHA | P. 69 | FHA | P. 69 | FHA | P. 69 |
| FHA | <50 | <50 | 400 | 100 | 1600 | 100 |
| P. 69 | <50 | <50 | <50 | 200 | 200 | 400 |
| OVA | <50 | <50 | <50 | <50 | 100 | 200 |

[a]Determined by Elisa
[b]Mice aerosol challenged d 14

There were no detectable antibodies against FHA of P.69 prior to aerosol challenge (d8). There were no anti-OVA antibodies to serum of OVA immunised mice (data not shown). Following challenge (>d14) the anti-FHA response did exhibit large increase in FHA immunised mice. This increase was specific, the anti-P.69 response did not increase proportionally in these mice. There was a small increase in anti-P.69 titre in P.69 immunised mice compared to FHA or P.69 immunised mice. This demonstrated that previous respiratory exposure to FHA and, possibly, P.69 can prime the mice to mount an amnestic response serum response upon contact with the pathogen.

EXAMPLE 2

Tetanus Component

Groups of 10 mice were immunised intranasally with one or two doses of 20 $\mu$g of C fragment or OVA as a control. 28 days after the final immunisation mice were challenged with 500 $LD_{50}$ of tetanus toxin and their survival monitored for 4 days, the results are shown in Table 2 below. Survival was enhanced in mice receiving 1 or 2 doses of C fragment compared to the control mice. All of the control mice were dead the day after challenge.

Protection was greatly enhanced by giving 2 doses of C fragment, by day 4 post-challenge 80% of the mice in the 2 dose group were still alive compared to 10% in the mice receiving a single dose.

TABLE 2

Protection of mice against tetanus toxin
challenge by I/N immunisation with C fragment

| Group | Dose | No of Mice | Survival post-challenge Day | | | |
|---|---|---|---|---|---|---|
| | | | 2 | 3 | 4 | 5 |
| 1. C-frag | 20 μg | 10 | 3 | 3 | 2 | 1 |
| 2. C-frag | 2 × 20 μg | 10 | 10 | 8 | 8 | 8 |
| 3. Ova | 2 × 20 μg | 10 | 0 | 0 | 0 | 0 |

Serum Response

The mice receiving 2 doses of C fragment had a mean serum anti-C fragment titre of greater than 200 prior to challenge.

MATERIALS AND METHODS

Antigens

P.69 was synthesised intracellularly in *E. coli* and purified as described in A. J. Makoff et al, *Bio/Technology* 8, 1030 (1990). FHA was provided by SKB under and exchange of reagents agreement. C fragment was produced from *E. coli* as in A. J. Makoff et al, *Bio/Technology* 7, 1043 (1989). Antigens were diluted in PBS immediately prior to immunisation.

Immunisation

Adult (6–8 weeks) BALB/c mice were anaesthetised with metathane. 30 μl of antigen solution was added to the external nares of mice (15 μl/nares) as they recovered consciousness. Antigen was taken into respiratory tract by inhalation.

Aerosol Challenge with *B. Pertussis*

Mice were placed in cages on a rotating carousel in a plastic exposure chamber as described in P. Novotny et al.

Development for Biological Standards, 61, 27 91985). A bacterial suspension in PBS was prepared from 2- to 3-day old cultures of *B. pertussis* BBC26 grown on CW blood agar plates. The mice were exposed to an aerosol (generated from the bacterial suspension) of $2\times10^9$ Colony-forming units (CFU) in PBS by a Turret mouthpiece tubing operated by a System 22 CR60 high-glow compressor (Medic-Aid), Pagham, West Sussex, UK) giving a very fine mist at a dynamic flow of 8.5 liters/min. The generated mist was drawn through a chamber by a vacuum pump at a passage of ca.12L of air per mist mixture per min, which maintained 70% relative humidity in the chamber. The exposure to aerosol lasted 30 min; a period of 10 min then allowed the chamber to clear.

The course of the infection was assessed by performing counts of viable bacteria in lungs. Groups of four mice were removed at intervals and killed by cervical dislocation, and their lungs were aseptically removed and homogenised in a Potter-Elvehjem homogenizer with 2 ml of PBS. Dilutions of the homogenate were spotted onto Cohen-Wheeler (CW) blood agar plates and the number of CFU was determined for each set of lungs.

Tetanus Challenge

Mice were challenged with 500 $LD_{50', m}$ of tetanus toxin subcutaneously and observed regularly for 5 days.

Elisa

Serum anti-P.69, anti-FHA and anti-C fragment antibodies were measured using an enzyme-linked immunosorbent assay (ELISA). Antigen (50 μl; 1 g/ml in phosphate-buffered saline, pH7.2) was absorbed onto 96-well microtitre plates (EIA 'Costar' NBL, Northumbria, UK) by incubation at 4° C. overnight. Wells were aspirated and washed three times with PBS containing 0.05% (v/v) Tween 20 (PBS-T; Sigma), and then blocked with 3% (w/v) bovine serum albumin (BSA; Sigma) in PBS. After washing, 50 μl of test serum appropriately diluted in PBS-T-0.1% BSA was added per well. After incubation at 37° C. for 2 h, the wells were washed and incubated at room temperature with 50 μl of substrate (0.04% O-phenylenediamine hydrochloride; Sigma) dissolved in phosphate citrate buffer (pH 5.0[24 mM citrate, 64 mM disodium hydrogen phosphate] containing 40 μl hydrogen peroxide). The reaction was terminated by the addition of 50 μl 1M sulphuric acid. Plates were read in a Titertek Multiscan MCC ELISA reader at 492 nm.

The titre was expressed as the reciprocal of the highest dilution of test serum that gave an absorbance reading twice that of the similarly diluted pre-bleed serum. Absorbance values below 0.1 were discarded.

ELSIPOT Assay for Specific Antibody Secreting Cells (ASC) in Murine Lungs.

Local antibody production in the murine lung was determined using the ELISPOT technique. Lymphocytes were isolated from murine lungs as follows: Lungs were washed briefly in PBS to remove traces of blood and then were finely chopped with a scalpel blade. 1 ml of PBS containing 10 mM $MgCl_2$, 0.5 U/ml collagenase A (Boehringer Mannheim, Lewes, UK) and 0.25 mg/ml DNase 1 (Boehringer) was added for each pair of lungs and incubated at 37° C. with gentle agitation for 45 min. The mixture was then passed through a 40 gauge mesh. Lumps were pressed through the mesh with the plunger from a 5 ml syringe. The cell suspension was placed in a centrifuge tube and allowed to stand for several minutes to allow large debris to settle. The supernatant was removed and the cells were pelletea and washed several times. Red cells and non-viable cells were removed by centrifugation on a Ficol-Isopaque gradient (LSM, Flow Laboratories Ltd, Herts, UK). After washing cell viability was determined by Trypan Blue exclusion. Cells were finally suspended in RPM11640 complete Medium (10% foetal calf serum, penicillin 100 IU/ml, streptomycin 100 g/ml, L-glutamine 2 mm; Flow).

The ELSIPOT assay was performed as follows. Briefly, 24-well tissue culture plates (Costar) were coated overnight with P.69, FHA or OVA (0.5 ml of 1 g.ml in PBA) after washing and blocking 0.5 ml volumes of dilutions of the lymphocyte suspension in complete $RPM_1$ 1640 were added to the wells and incubated at 37° C./10% $C_2$ for 3 h. After washing goat anti-mouse IgG, A or M (1/1000, Sigma) and rabbit anti-goat IgG-alkaline phosphatase (1/1000, Sigma) were added sequentially. Finally, substrate solution (0.5 μl of 1 mg/ml 5-bromo-4-chloro-3-indolyl phosphate (BCIP) in 2-amino-2-methyl-1,3-propanediol (AMP) buffer, Sigma) was added and plates were incubated until blue spots were visible under low power microscopy.

What is claimed is:

1. A method for immunizing a host against tetanus infection, which method consists of administering directly to a mucosal surface of said host, by intranasal administration, in an amount effective to induce an immune response in said surface, an acellular vaccine composition comprising:

(a) a mucosally immunogenically active substance consisting of the 50 kD C fragment of tetanus toxin, or an immunoprotective fragment thereof having the ability to bind eukaryotic cells possessing the trisialoganlioside G16 and the ability to elicit protection in mice against lethal challenge with tetanus toxin, and (b) a pharmaceutically acceptable carrier.

2. A method according to claim 1, wherein the acellular vaccine composition is administered in the form of nasal drops, or a nasal spray, or dry powder for inhalation.

3. A method according to claim 2, wherein the vaccine composition is in the form of nasal drops comprising an aqueous solution additionally containing one or more excipients selected from preservatives, viscosity adjusting agents, tonicity adjusting agents and buffering agents.

4. A method according to claim 1, wherein the host is a mammal.

5. A method according to claim 4, wherein the mammal is a human.

6. A method according to claim 1, wherein a dose in the range from about 1 to 100 microgrammes of the 50 kD C fragment of tetanus toxin is administered to the host.

7. A method of immunizing a host against tetanus and *B. pertussis* infection with method consisting of administering directly to a mucosal surface of said host by intranasal administration, an amount effective to induce an immune response in said surface, an acellular vaccine composition comprising:

(a) a mucosally immunogenically active substance consisting of 50 kD C fragment of tetanus toxin or an immunoprotective fragment thereof having the ability to bind eukaryotic cells possessing the trisialoganglioside $G_T16$ and the ability to elicit protection in mice against lethal challenge with tetanus toxin;

(b) a mucosally immunogenically active substance comprising the P69 outer membrane protein of *B. pertussis* or immunoprotective fragment thereof having the ability to elicit protection in mice against challenge with *B. pertussis*; and (c) a pharmaceutically acceptable carrier.

8. A method according to claim 7, wherein the acellular vaccine composition further comprises:

a mucosally immunogenically active substance comprising *B. pertussis* filamentous haemagglutinin or an immunoprotective fragment thereof having the ability to elicit protection in mice against challenge with *B. pertussis*.

9. A method according to claim 7, wherein the acellular vaccine composition is administered in the form of nasal drops, or a nasal spray or dry powder for inhalation.

10. A method according to claim 9, wherein the vaccine composition is in the form of nasal drops comprising an aqueous solution additionally containing one or more excipients selected from preservatives, viscosity adjusting agents, tonicity adjusting agents and buffering agents.

11. A method according to claim 8, wherein the acellular vaccine composition is administered in the form of nasal drops, or a nasal spray or dry powder for inhalation.

12. A method according to claim 7, wherein a dose in the range from about 1 to 100 microgrammes of the 50 kD C fragment of tetanus toxin, or an immunoprotective fragment thereof having the ability to bind eukaryotic cells possessing the trisialoganglioside $G_T16$ and the ability to elicit protection in mice against lethal challenge with tetanus toxin, and a dose in the range from about 1 to 100 microgrammes of the P69 outer membrane protein of *B. pertussis*, or an immunoprotective fragment thereof having the ability to elicit protection in mice against challenge with *B. pertussis*, are administered to the host.

13. A method of immunizing a host against tetanus and *B. pertussis* infection, which method consists of administering directly to a mucosal surface of said host, by intranasal administration, in an amount effective to induce an immune response in said surface, an acellular vaccine composition comprising;

(a) the 50kD C fragment of tetanus toxin;

(b) the P69 outer membrane protein of B. pertussis;

(c) *B. pertussis* filamentous haemagglutinin; and (d) a pharmaceutically acceptable carrier.

14. A method according to claim 13, wherein each of (a), (b) and (c) are administered in a dose of from about 1 to 100 microgrammes.

15. An acellular intranasal vaccine composition in the form of nasal drops, a nasal spray or a dry powder for inhalation comprising:

(a) the 50 kD C fragment of tetanus toxin;

(b) the P69 outer membrane protein of *B. pertussis;*

(c) *B. pertussis* filamentous haemagglutinin; and (d) a pharmaceutically acceptable carrier.

16. An acellular intranasal vaccine composition according to claim 15, which is in the form of nasal drops comprising an aqueous solution additionally containing one or more excipients selected from preservatives, viscosity adjusting agents, tonicity adjusting agents and buffering agents.

\* \* \* \* \*